US006893817B2

(12) United States Patent
Berghof et al.

(10) Patent No.: US 6,893,817 B2
(45) Date of Patent: *May 17, 2005

(54) AMINO ACID SEQUENCES AND METHOD FOR ISOLATING BACTERIES FROM THE TYPE GENUS PSEUDOMONAS

(75) Inventors: Cornelia Berghof, Berlin (DE); Alexander Gasch, Berlin (DE); Anja Braeuer, Berlin (DE); Cordt Groenewald, Berlin (DE); Freimut Wilborn, Berlin (DE); Arndt Rolfs, Rostock (DE)

(73) Assignee: Biotecon Diagnostics GmbH, Berlin (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/508,238

(22) PCT Filed: Sep. 9, 1998

(86) PCT No.: PCT/EP98/05738

§ 371 (c)(1),
(2), (4) Date: May 8, 2000

(87) PCT Pub. No.: WO99/12949

PCT Pub. Date: Mar. 18, 1999

(65) Prior Publication Data

US 2003/0082656 A1 May 1, 2003

(30) Foreign Application Priority Data

Sep. 9, 1997 (DE) .......................... 197 39 611

(51) Int. Cl.$^7$ .......................... C12Q 1/68; C12P 19/34; C07H 21/04
(52) U.S. Cl. .................. 435/6; 435/91.1; 435/91.2; 536/23.1; 536/24.3
(58) Field of Search .................. 435/6, 91.1, 91.2; 536/23.1, 24.3

(56) References Cited

U.S. PATENT DOCUMENTS

| 5,714,321 A | * | 2/1998 | Hogan et al. .................. 435/6 |
| 5,783,182 A | * | 7/1998 | Thompson .............. 424/93.21 |
| 6,191,268 B1 | * | 2/2001 | Liskay et al. .............. 536/23.5 |
| 6,194,145 B1 | * | 2/2001 | Heidrich et al. .............. 435/6 |

FOREIGN PATENT DOCUMENTS

WO    WO 93/11264    *    6/1993 .................. 435/6

OTHER PUBLICATIONS

Rijpkema et al; J. Clin. Microb. vol. 33, pp. 3091–3095, 1995.*
Tyler et al, Clinical and Diagnostic Laboratory Immunology; vol. 2, pp. 448–453, 1995.*
Kur et al; Acta Microbiologica Polonica, vol 44, pp. 111–117, 1995.*
Accession No. AC1221451, Genbank, 2002.*
EST accession No. AA535879 Aug. 21, 1997.*
Kur et al., Acta Microbiologica Polonica; vol. 44, pp 111–117; 1995.*
Ahern, Holly; The Scientist, vol. 9, 1995, from the Internet pp 1–5.*
Mantynen et al, International Journal of Food Microbiology, vol. 36, pp 135–143, 1997; sequence provided.*
Rink et al., Chemical Research in Toxicology; vol. 9, pp 382–389, 1996; sequence provided.*
Smith et al., Journal of Biological Chemistry, 1990, vol 265, pp 13335–13343.*

* cited by examiner

Primary Examiner—Jehanne Sitton
(74) Attorney, Agent, or Firm—Frommer Lawrence & Haug LLP; Ronald R. Santucci

(57) ABSTRACT

The present invention relates to a nucleic acid molecule or molecules and to a process for the detection of bacteria of the *Pseudomonas* genus, especially *Pseudomonas aeruginosa*. The invention relates also to a test kit or kits for carrying out the said detection processes.

28 Claims, No Drawings

SEQUENCE LISTING

<160> NUMBER OF SEQ ID NOS: 5

<210> SEQ ID NO 1
<211> LENGTH: 131
<212> TYPE: DNA
<213> ORGANISM: Pseudomonas
<220> FEATURE:
<221> NAME/KEY: misc_feature
<222> LOCATION: (21)
<223> OTHER INFORMATION: N=Y

<400> SEQUENCE: 1
ataacaccca aacaatctga ngattgtgtg ttgtaaggtg aagtcgacga accgaaagtt      60
cgcatgaacc gcaaacacct tgaaatcaca tacctgaatc cggatagacg taagcccaag     120
cgaacggata t                                                          131

<210> SEQ ID NO 2
<211> LENGTH: 20
<212> TYPE: DNA
<213> ORGANISM: Pseudomonas

<400> SEQUENCE: 2
gataggctgg gtgtgtaagc                                                  20

<210> SEQ ID NO 3
<211> LENGTH: 20
<212> TYPE: DNA
<213> ORGANISM: Pseudomonas

<400> SEQUENCE: 3
cttgggctta cgtctatccg                                                  20

<210> SEQ ID NO 4
<211> LENGTH: 23
<212> TYPE: DNA
<213> ORGANISM: Pseudomonas

<400> SEQUENCE: 4
ttcaggtatg tgatttcaag gtg                                              23

<210> SEQ ID NO 5
<211> LENGTH: 23
<212> TYPE: DNA
<213> ORGANISM: Pseudomonas

<400> SEQUENCE: 5
gacgattgtg tgttgtaagg tga                                              23

AMINO ACID SEQUENCES AND METHOD FOR ISOLATING BACTERIES FROM THE TYPE GENUS PSEUDOMONAS

The invention relates to nucleic acid molecules for detecting *Pseudomonas*, to a kit and to uses thereof.

GENERAL BACKGROUND OF THE INVENTION

The gram-negative bacterium *Pseudomonas aeruginosa* is a widespread bacterium that is pathogenic for humans and that constitutes a major health risk especially to neonates and to people having weakened resistance. Besides its major clinical significance, the antibiotic resistances that are frequently present and the formation of toxins, especially the highly toxic exotoxin A (Woods, D. E. and Iglewski, B. H., Rev. Infect. Dis. 5, 714–722 (1983), *Pseudomonas aeruginosa* is one of the most important bacterial causes of cases of food poisoning. Conventional processes require at least 4 days for the detection of *Pseudomonas aeruginosa*. There is therefore an urgent need for the development of rapid processes for detecting *Pseudomonas aeruginosa* in food and in clinical samples.

In recent years, a number of new methods have been developed for routine use in detecting particular microorganisms. These include immunological processes based on the use of polyvalent or monoclonal antibodies and processes in which nucleic acid probes are used for detection by means of hybridisation to organism-specific nucleic acids. Further methods that have been described are those processes which are based on a specific nucleic acid amplification, with or without a subsequent confirmation reaction by nucleic acid hybridisation. Processes used for the amplification of nucleic acids are, for example, the polymerase chain reaction (PCR) [U.S. Pat. Nos. 4,683,195; 4,683,202; and 4,965,188], the ligase chain reaction [WO Publication 89/09835], "self-sustained sequence replication" [EP 329,822], the "transcription based amplification system" [EP 310,229] and the Qβ RNA-replicase system [U.S. Pat. No. 4,957,858].

The mentioned nucleic-acid-based processes are so sensitive that, in contrast to conventional microbiological processes, it is possible to dispense with, or considerably curtail, a lengthy increase in quantity of the microorganism being detected from the sample under investigation. Testing for the presence or absence of the microorganism in question is therefore generally concluded within one day when using the mentioned nucleic-acid-based processes, thereby achieving a considerable reduction in time, especially when conventional processes require several days or weeks for detection.

Various PCR-based processes for the detection of *Pseudomonas aeruginosa* have been described. By amplifying a region of DNA having a length of 369 bp from the exotoxin A gene it has been possible to detect the presence of strains of the species *Pseudomonas aeruginosa* selectively [Khan et al. (1994), Appl. Environ. Microbiol. 60, 3739–3745]. Even though no bacteria of other species were detected using that PCR system, an amplified product was observed in only 96% of the 130 *Pseudomonas aeruginosa* strains tested in total. Consequently, that PCR system is of only limited suitability for establishing a rapid process by means of which the presence of all strains of *Pseudomonas aeruginosa* can be detected reliably.

With the aid of a further, recently published process based on a multiplex PCR it has been possible to detect, selectively, fluorescent pseudomonads on the one hand and *Pseudomonas aeruginosa* on the other hand [De Vos et al. (1997), J. Clin. Microbiol. 35, 1295–1299]. Using that process, it was possible to detect each of the 150 isolates of *Pseudomonas aeruginosa* tested in total. It is, however, disadvantageous that the oprL gene used for the selective detection of *Pseudomonas aeruginosa* is also highly conserved in other species of the *Pseudomonas* genus. Thus, the amino acids that are coded for in the region of the binding sites of the primers used by Voss et al. are identical in *Pseudomonas putida* and *Pseudomonas aeruginosa*. The detection of *Pseudomonas aeruginosa* is accordingly based merely on a few different base pairs caused by the variation in the third position of particular amino acid codons, which on the basis of experience carries a high risk of false-positive and/or false-negative results occurring.

In addition, because of the high degree of conservation of the oprI and oprL genes, the multiplex PCR system described is unlikely to offer a possible means of detecting— for example by the use of various probes subsequently to the PCR reaction—other clinically significant species of the *Pseudomonas* genus, such as, for example, *Pseudomonas fluorescens*, *Pseudomonas mendocina*, *Pseudomonas putida* or *Pseudomonas stutzeri*.

An aim of the invention described herein was to establish nucleic acid sequences whose use as primers and/or probes would ensure detection, in as complete a manner as possible, of all representatives of the species *Pseudomonas aeruginosa*. A further aim of the invention was to identify a region of the genome having sufficiently high sequence variability within different species of the *Pseudomonas* genus to allow, optionally, the detection of other species of the *Pseudomonas* genus as well, for example by using different variants of primers and/or probes in the PCR or subsequently to the PCR.

Depending on the size of the group of microorganisms to be detected and the evolutionary relatedness (similarity) of microorganisms to be excluded (that are not to be detected), detection based on differential DNA sequences requires very extensive preliminary work in order to identify suitable DNA sequences that have the desired specificity in the particular case. The invention described herein relates to such DNA sequences, by means of which the rapid detection of bacteria of the *Pseudomonas* genus, especially of *Pseudomonas aeruginosa*, is possible.

Also known are nucleic acid molecules that can be used as probes or primers for the detection of microoganisms, especially for the detection of *Pseudomonas aeruginosa* (WO 96/00298 and Acta Microbiologica Polonica, 44 (1995) 111–117) the nucleic acid molecules being obtained from the 16S–23S intergenic region. Accordingly, it is possible for *Pseudomonas aeruginosa* to be distinguished from other *Pseudomonas* species and also from bacteria of other genera.

It is also known that, for bacteria that do not belong to *Pseudomonas* species, the 23S–5S intergenic region can be successfully used for isolating species- and genera-specific nucleic acid molecules (J. Applied Bakteriology, 80 (1996) 244–251 and EP 0 739 988).

DESCRIPTION OF THE INVENTION

The problem underlying the invention is solved, according to one embodiment, by a nucleic acid molecule that is obtainable by starting from a plurality of strains belonging to, on the one hand, a to-be-detected group of bacteria of the *Pseudomonas* genus and, on the other hand, not-to-be-detected bacteria, (a) isolating, in a manner known per se, genomic DNA from a *Pseudomonas* strain of those groups (first strain), (b) amplifying, in a manner known per se, the 23S/5S intergenic region, optionally together with the directly adjacent 23S region and/or the directly adjacent 5S region, and obtaining the amplification product (first amplification product),
(c) in accordance with steps (a) and (b) in each case, isolating genomic DNA using a second, third, . . . and/or $n^{th}$ Pseudomonas strain of those groups, amplifying the 23S/5S intergenic region, optionally together with the directly adjacent 23S region and/or the directly adjacent 5S region, and obtaining the amplification product (second, third, . . . $n^{th}$ amplification product),
(d) determining, in a manner known per se, the DNA sequence of amplification products obtained according to (b) and (c), and comparing the DNA sequence of the amplification product according to (b) with the DNA sequence of one or more amplification products according to (c), and
(e) obtaining, as a primer or probe, in a manner known per se, a nucleic acid molecule by means of which the to-be-detected group of bacteria of the Pseudomonas genus can be distinguished from the not-to-be-detected group of bacteria of the Pseudomonas genus on the basis of differences at at least one nucleotide position in the sequence region of the nucleic acid molecule.

The nucleic acid molecule according to the invention can be obtainable by starting from strains belonging to, on the one hand, to-be-detected bacteria of the Pseudomonas genus and, on the other hand, not-to-be-detected bacteria of a genus (genera) other than Pseudomonas.

The problem underlying the invention is solved, according to a further embodiment, by a nucleic acid molecule that is obtainable by starting from a plurality of strains belonging to a to-be-detected group and a not-to-be-detected group of bacteria of the Pseudomonas genus,
(a) isolating, in a manner known per se, genomic DNA from a Pseudomonas strain of those groups (first strain),
(b) amplifying, in a manner known per se, the 23S/5S intergenic region, optionally together with the directly adjacent 23S region and/or the directly adjacent 5S region, and obtaining the amplification product (first amplification product),
(c) in accordance with steps (a) and (b) in each case, isolating genomic DNA using a second, third, . . . and/or $n^{th}$ Pseudomonas strain of those groups, amplifying the 23S/5S intergenic region, optionally together with the directly adjacent 23S region and/or the directly adjacent 5S region, and obtaining the amplification product (second, third, . . . $n^{th}$ amplification product),
(d) determining, in a manner known per se, the DNA sequence of amplification products obtained according to (b) and (c), and comparing the DNA sequence of the amplification product according to (b) with the DNA sequence of one or more amplification products according to (c), and
(e) obtaining, as a primer or probe, in a manner known per se, a nucleic acid molecule by means of which the to-be-detected group of bacteria of the Pseudomonas genus can be distinguished from the not-to-be-detected group of bacteria of the Pseudomonas genus on the basis of differences at at least one nucleotide position in the sequence region of the nucleic acid molecule.

The nucleic acid molecule according to the invention can be obtainable by starting from strains belonging to a to-be-detected group of bacteria of the species Pseudomonas aeruginosa and a not-to-be-detected group of bacteria of other species.

The invention relates also to a nucleic acid molecule of SEQ ID NO 1 or the sequence complementary thereto.

The invention relates also to a nucleic acid molecule of that kind, having a shortened sequence compared with the aforementioned nucleic acid molecule, namely the sequence of the region or in the region of the nucleotide positions 12 to 131.

The invention relates also to a nucleic acid molecule of that kind, having a shortened sequence compared with a nucleic acid molecule of SEQ ID NO 1, namely
(i) SEQ ID NO 3 or
(ii) SEQ ID NO 4 or
(iii) SEQ ID NO 5 or
(iv) the sequence complementary to each of (i), (ii) and (iii).

The invention relates also to a nucleic acid molecule of SEQ ID NO 2 or the sequence complementary thereto.

A nucleic acid molecule according to the invention may be characterised in that, in respect of its sequence in at least 10 successive nucleotides of its nucleotide chain,
(i) it is identical to a nucleic acid molecule according to one of the preceding claims or
(ii) it corresponds to a nucleic acid molecule according to one of the preceding claims in 9 out of 10 successive nucleotides or
(iii) it corresponds to a nucleic acid molecule according to one of the preceding claims in 8 out of 10 successive nucleotides or
(iv) it is at least 90% homologous to a nucleic acid molecule according to one of the preceding claims.

Such a nucleic acid molecule according to the invention can be characterised in that it is from 10 to 250, and preferably from 15 to 30, nucleotides long.

A nucleic acid molecule according to the invention can be characterised in that it is single-stranded or double-stranded.

A nucleic acid molecule according to the invention can be characterised in that it is present
(i) as DNA or
(ii) as RNA corresponding to (i) or
(iii) as PNA,
the nucleic acid molecule where appropriate having been modified in a manner known per se for analytical detection processes, especially those based on hybridisation and/or amplification.

Thus, a nucleic acid molecule according to the invention can have been modified in such a manner that up to 20% of the nucleotides of at least 10 successive nucleotides of its nucleotide chain, especially 1 or 2 nucleotides, have been replaced by analogous building blocks known per se as probes and/or primers, especially by nucleotides that do not occur naturally in bacteria.

The nucleic acid molecule according to the invention can also have been modified or labelled or additionally modified or labelled in such a manner that it comprises, in a manner known per se for analytical detection processes, one or more radioactive groups, coloured groups, fluorescent groups, groups for immobilisation on a solid phase and/or groups for an indirect or direct reaction, especially for an enzymatic reaction, preferably using antibodies, antigens, enzymes and/or substances having an affinity for enzymes or enzyme complexes, and/or otherwise modifying or modified groups of nucleic-acid-like structure.

According to a further embodiment, the problem underlying the invention is solved by a kit for analytical detection processes, especially for the detection of bacteria of the Pseudomonas genus, that kit being characterised by one or more nucleic acid molecules according to the invention.

According to a further embodiment, the problem underlying the invention is solved by use of one or more nucleic acid molecules according to the invention or of a kit according to the invention for detection of the presence or absence of bacteria belonging to a group of bacteria of the Pseudomonas genus.

The use according to the invention can be characterised in that the group of bacteria of the Pseudomonas genus includes various strains of *Pseudomonas aeruginosa* or is made up from those strains.

Such use according to the invention can be characterised in that the group of bacteria of the *Pseudomonas* genus is composed exclusively of *Pseudomonas aeruginosa* strains.

Use according to the invention can also be characterised in that nucleic acid hybridisation and/or nucleic acid amplification is/are carried out.

Use according to the invention can also be characterised in that, as nucleic acid amplification, a polymerase chain reaction is carried out.

Use according to the invention can also be characterised in that the detection is carried out by distinguishing the to-be-detected bacteria from not-to-be-detected bacteria on the basis of differences in the genomic DNA and/or RNA at at least one nucleotide position in the region of a nucleic acid molecule according to the invention.

Use according to the invention can also be characterised in that distinguishing is carried out on the basis of differences in the region of a nucleic acid molecule of SEQ ID NO 1 or of its complementary sequence.

To detect specific microorganisms by means of nucleic acid hybridisation or amplification, organism-specific oligonucleotides are, therefore, used according to the invention. Organism-specific oligonucleotides are nucleic acids, from 10 to 250 bases (preferably from 15 to 30 bases) long, the base sequence of which is characteristic of a specific microorganism or a group of microorganisms. When using such organism-specific oligonucleotides (for example, as primers or probes) with the processes mentioned hereinbefore, hybridisation to DNA/amplification of DNA can take place, under suitable reaction conditions, only when the DNA of the microorganisms to be detected in the particular case is present.

Procaryotic ribosomes comprise three distinct nucleic acid components, which are generally known as 5S, 16S and 23S rRNA (ribosomal ribonucleic acid). The genetic information for those ribonucleic acids (rDNA) is arranged in the genome typically in the form of tandems. The organisation of such a unit is 16S-23S-5S, the three genes being separated from one another by short hypervariable intergenic regions. The units are present in the genome in several copies, it being possible for the number of the repeating units to vary in different bacteria. The high degree of conservation of the DNA sequence in the region of 16S rDNA, 23S rDNA and 5S rDNA across the entire kingdom of bacteria allows non-specific oligonucleotides to be designed, even without precise knowledge of the DNA sequences of the microorganisms to be investigated. Such non-specific oligonucleotides are characteristic of a relatively large group of microorganisms, which are generally pylogenetically related. By using those non-specific oligonucleotides it will be possible for the person skilled in the art, for example after appropriate preliminary tests by means of DNA amplification using PCR, to isolate rDNA fragments, for example the 23S/5S intergenic region, of any particular microorganism. By DNA sequencing, it is then possible to determine the sequence of the hypervariable intergenic regions of the microorganism in question.

DNA sequencing of the 23S/5S intergenic region of as large a number as possible of to-be-detected bacteria (e.g. of various *Pseudomonas* species), on the one hand, and subsequent comparison of those DNA sequences, on the other hand, allows DNA regions to be identified that in the group investigated (e.g. all *Pseudomonas* species) are not changed or only insignificantly changed.

DNA sequencing of the 23S/5S intergenic region of selected not-to-be-detected bacteria (e.g. bacteria that do not belong to the *Pseudomonas* genus), on the one hand, and subsequent comparison of those DNA sequences with the sequences of to-be-detected bacteria (e.g. various *Pseudomonas* species), on the other hand, allows DNA sequences to be identified that are characteristic of the to-be-detected bacteria (e.g. all *Pseudomonas* species). It is then possible to derive, from these DNA sequences, oligonucleotides that can be used as primers and/or probes in processes based on nucleic acids, with the aim of specifically detecting the group of bacteria in question (e.g. all species of the *Pseudomonas* genus).

The DNA sequences described in the present invention for detecting bacteria of the *Pseudomonas* genus, especially bacteria of the species *Pseudomonas aeruginosa*, are based on the 23S/5S intergenic region and the directly adjacent region of the 23S rDNA. The DNA sequence in that region was determined for a large number of bacteria. After exact sequence comparisons, organism-specific nucleic acid sequences were determined, which can be used for primers and/or probes for use in a species-/genus-specific detection process.

To detect the group of microorganisms in question, nucleic acids, preferably genomic DNA, are firstly released from the cells contained in a sample or bacterial culture to be investigated. By means of nucleic acid hybridisation, it is then possible—using the organism-specific oligonucleotides according to the invention as a probe—to directly detect organism-specific nucleic acids in the sample to be investigated. Various processes known to the person skilled in the art are suitable for that purpose, such as, for example, "Southern blot" or "dot blot".

Preference is given, however, above all on account of the relatively high sensitivity, to an indirect detection process in which the DNA/RNA sequences sought are firstly amplified by means of the above-mentioned processes for amplifying nucleic acids, preferably PCR.

The amplification of DNA/RNA using the processes mentioned can be effected by using organism-specific oligonucleotides as primers, specific amplification products being formed only when DNA/RNA of the to-be-detected microorganism is present. The specificity of the detection process can be increased by a subsequent detection reaction using organism-specific oligonucleotides as probes. For that subsequent detection reaction it is also possible to use non-specific oligonucleotides.

Alternatively, the nucleic acid amplification can also be carried out in the presence of one or more non-specific oligonucleotides, so that it is possible that DNA/RNA of other, not-to-be-detected microorganisms may also be amplified. Such an amplification process is generally less specific and should therefore be backed up by a subsequent detection reaction using one or more organism-specific oligonucleotide(s) as probe(s).

Various processes by which the amplification products formed in the indirect processes can be detected will be known to the person skilled in the art. These include, inter alia, visualisation by means of gel electrophoresis, the hybridisation of probes on immobilised reaction products [coupled to nylon or nitrocellulose filters ("Southern blots") or, for example, on beads or microtitre plates] and the hybridisation of the reaction products on immobilised probes (e.g. "reverse dot blots" or beads or microtitre plates coupled with probes).

A large number of different variants have been described by means of which organism-specific oligonucleotides (for example probes and primers) can be labelled or modified for the direct or indirect detection processes described. They may comprise, for example, radioactive, coloured, fluorescent or otherwise modified or modifying groups, for example antibodies, antigens, enzymes or other substances having an affinity for enzymes or enzyme complexes. Probes and primers may be either naturally occurring or synthetically produced double-stranded or single-stranded DNA or RNA or modified forms of DNA or RNA, such as, for example, PNA (in these molecules the sugar units have been replaced by amino acids or peptides). Particular nucleotides or a number of nucleotides of the probes or primers may be replaced by analogous building blocks (such as, for example, nucleotides that do not naturally occur in the target nucleic acid). In the case of the above-mentioned indirect detection processes, detection can be carried out also by means of an internally labelled amplification product. That can be effected, for example, by integrating modified nucleoside triphosphates (for example, coupled with digoxygenin or fluorescein) during the amplification reaction.

Suitable organism-specific oligonucleotides according to the invention are nucleic acids, preferably from 10 to 250 bases and especially from 15 to 30 bases long, that correspond, at least in a 10 base long sequence, to Sequences 1 to 5 mentioned hereinbelow or to their complementary sequences. Relatively small differences (1 or 2 bases) in that 10 base long sequence are possible without the specificity mentioned in the particular case being lost in amplification and/or hybridisation. The person skilled in the art will know that in the case of such relatively small differences the reaction conditions will need to be altered accordingly; cf., for example, T. Maniatis, Molecular Cloning, Editors G. Sambrook & E. F. Fritsch, Cold Spring Harbour Laboratory Press, 1989.

The sequence of *Pseudomonas aeruginosa* (ATCC 10145) in the region of the 23S/5S intergenic region is:

```
                                  (Sequence 1 = SEQ ID NO 1))
ATAACACCCAAACAATCTGAYGATTGTGTGTTGTAAGGTGAAGTCGACGA

ACCGAAAGTTCGCATGAACCGCAAACACCTTGAAATCACATACCTGAATC

CGGATAGACGTAAGCCCAAGCGAACGGATAT
```

In addition, the sequence in the region of the 23S/5S intergenic region was determined for 6 further strains of the species *Pseudomonas aeruginosa* and for at least one strain of each of the following species: *Pseudomonas asplenii, Pseudomonas citronellosis, Pseudomonas corrugate, Pseudomonas fluorescens, Pseudomonas fragi, Pseudomonas mendocina, Pseudomonas pseudoalcaligenes, Pseudomonas putida, Pseudomonas stutzeri, Pseudomonas syringae*. The sequence comparisons showed that a number of oligonucleotides derived from Sequence 1 are suitable for the selective detection of bacteria of the species *Pseudomonas aeruginosa*. The sequence of the region (12–131) is suitable for such organism-specific oligonucleotides.

From Sequence 1 there were derived the following oligonucleotides, which are especially suitable as primers for PCR (Sequence 3 and 5) and as a probe (Sequence 4).

Oligonucleotide Pa1 (Sequence 2) corresponds to position 2823–2842 of a 23S rRNA gene of *Pseudomonas aeruginosa* ATCC 10145 [Toschka et al. (1987), Nucleic Acids. Res. 15, 7182]:

```
Oligonucleotide Pa1: (Sequence 2 = SEQ ID NO 2)
5'-GATAGGCTGGGTGTGTAAGC-3'

Oligonucleotide Pa2: (Sequence 3 = SEQ ID NO 3)
5'-CTTGGGCTTACGTCTATCCG-3'

Oligonucleotide Pa3: (Sequence 4 = SEQ ID NO 4)
5'-TTCAGGTATGTGATTTCAAG GTG-3'

Oligonucleotide Pa4: (Sequence 5 = SEQ ID NO 5)
5'-GACGATTGTGTGTTGTAAGGTGA
```

EXAMPLE 1

Detection of Bacteria of the Species *Pseudomonas aeruginosa* Using the Polymerase Chain Reaction DNA was isolated by standard processes from pure cultures of the bacteria listed in Table 1. Approximately from 10 to 100 ng of each of those DNA preparations was then used in the PCR in the presence of 0.4 μM of each of oligonucleotide Pa1 and Pa2 or Pa4 and Pa2, 200 μM of dNTP's (Boehringer Mannheim), 4 mM $MgCl_2$, 16 mM $(NH_4)_2SO_4$, 67 mM Tris/HCl (pH 8.8), 0.01% Tween 20 and 0.03 U/μl Taq-polymerase (Biomaster). The PCR was carried out in a Perkin-Elmer 9600 (Pa1 and Pa2)/Biometra TRIO-Thermoblock (Pa4 and Pa2) thermocycler using the following thermoprofiles:

a) amplification using oligonucleotide Pa1 and Pa2

| | | |
|---|---|---|
| initial denaturing | 95° C. | 5 min |
| 1st amplification (15 cycles) | 94° C. | 35 sec |
| | 68° C. | 30 sec |
| | 72° C. | 30 sec |
| 2nd amplification (20 cycles) | 94° C. | 35 sec |
| | 64° C. | 30 sec |
| | 72° C. | 30 sec |
| final synthesis | 72° C. | 5 min | b) amplification using oligonucleotide Pa4 to Pa2

| | | |
|---|---|---|
| initial denaturing | 95° C. | 5 min |
| amplification (35 cycles) | 95° C. | 30 sec |
| | 62° C. | 30 sec |
| | 72° C. | 20 sec |
| final synthesis | 72° C. | 5 min |

After the end of the PCR reaction, the amplification products were separated by means of agarose gel electrophoresis and visualised by staining with ethidium bromide. The expected products having a length of 191 bp/102 bp were observed only in those cases in which DNA of strains of the species *Pseudomonas aeruginosa* was present (compare Table 1), but not in the presence of DNA of other tested bacteria. After the end of the run, the DNA contained in the gels was transferred by standard methods to nylon filters and hybridised with the oligonucleotide Pa3 (Sequence 4) biotinylated at the 5' terminus, in order to check the specificity. Hybridisation was effected in 5×SSC, 2% blocking reagent, 0.1% lauryl sarcosine, 0.02% SDS and 5 pmol/ml of probe for 4 hours at 48° C. Washing was carried out in 2×SSC, 0.1% SDS for 2×15 minutes at room temperature and in 2×SSC, 0.1% SDS for 1×15 minutes at 48° C. Detection was carried out according to standard methods using alkaline phosphatase conjugates (Extravidin, SIGMA, # E-2636) in the presence of 5-bromo-4-chloro-3-indolyl phosphate and 4-nitro-blue tetrazolium chloride (Boehringer Mannheim).

A band was observed on the filters only in those cases in which a band had previously been visible on the agarose gel (see Table 1). Thus, the presence of all the 86 tested *Pseudomonas aeruginosa* strains was detected by PCR and by hybridisation. In contrast, none of the tested bacterial strains not belonging to that species was detected using this system.

TABLE 1

Results of PCR amplification using the oligo-
nucleotides Pa1/Pa2 (SEQ ID NO 2 and SEQ ID NO 3) and Pa4/Pa2
(SEQ ID NO 5 and SEQ ID NO 3) and subsequent hybridisation
using the oligonucleotide PA3 (SEQ ID NO 4).

| Species | Designation of strain | Pa1/Pa2 | Pa4/Pa2 |
|---|---|---|---|
| *Pseudomonas aeruginosa* | ATCC 9027 | + | + |
| *Pseudomonas aeruginosa* | ATCC 10145 | + | + |
| *Pseudomonas aeruginosa* | ATCC 14886 | + | + |

TABLE 1-continued

Results of PCR amplification using the oligonucleotides Pa1/Pa2 (SEQ ID NO 2 and SEQ ID NO 3) and Pa4/Pa2 (SEQ ID NO 5 and SEQ ID NO 3) and subsequent hybridisation using the oligonucleotide PA3 (SEQ ID NO 4).

| Species | Designation of strain | Pa1/Pa2 | Pa4/Pa2 |
|---|---|---|---|
| Pseudomonas aeruginosa | ATCC 15522 | + | + |
| Pseudomonas aeruginosa | ATCC 15691 | + | + |
| Pseudomonas aeruginosa | ATCC 15692 | + | + |
| Pseudomonas aeruginosa | ATCC 21472 | + | + |
| Pseudomonas aeruginosa | ATCC 21776 | + | + |
| Pseudomonas aeruginosa | ATCC 33350 | + | + |
| Pseudomonas aeruginosa | ATCC 33361 | + | + |
| Pseudomonas aeruginosa | ATCC 33818 | + | + |
| Pseudomonas aeruginosa | ATCC 33988 | + | + |
| Pseudomonas aeruginosa | LMG 8029 | + | + |
| Pseudomonas aeruginosa | DSM 288 | + | + |
| Pseudomonas aeruginosa | DSM 939 | + | + |
| Pseudomonas aeruginosa | DSM 1117 | + | + |
| Pseudomonas aeruginosa | DSM 1253 | + | + |
| Pseudomonas aeruginosa | DSM 1299 | + | + |
| Pseudomonas aeruginosa | BC 682 | + | + |
| Pseudomonas aeruginosa | BC 4283 | + | + |
| Pseudomonas aeruginosa | BC 4880 | + | + |
| Pseudomonas aeruginosa | BC 4937 | + | + |
| Pseudomonas aeruginosa | BC 4938 | + | + |
| Pseudomonas aeruginosa | BC 5258 | + | + |
| Pseudomonas aeruginosa | BC 5594 | + | + |
| Pseudomonas aeruginosa | BC 5595 | + | + |
| Pseudomonas aeruginosa | BC 5596 | + | + |
| Pseudomonas aeruginosa | BC 5597 | + | + |
| Pseudomonas aeruginosa | BC 5598 | + | + |
| Pseudomonas aeruginosa | BC 5599 | + | + |
| Pseudomonas aeruginosa | BC 5600 | + | + |
| Pseudomonas aeruginosa | BC 5601 | + | + |
| Pseudomonas aeruginosa | BC 5602 | + | + |
| Pseudomonas aeruginosa | BC 5603 | + | + |
| Pseudomonas aeruginosa | BC 5604 | + | + |
| Pseudomonas aeruginosa | BC 5606 | + | + |
| Pseudomonas aeruginosa | BC 5607 | + | + |
| Pseudomonas aeruginosa | BC 5917 | + | + |
| Pseudomonas aeruginosa | BC 5918 | + | + |
| Pseudomonas aeruginosa | BC 5919 | + | + |
| Pseudomonas aeruginosa | BC 5920 | + | + |
| Pseudomonas aeruginosa | BC 5921 | + | + |
| Pseudomonas aeruginosa | BC 5922 | + | + |
| Pseudomonas aeruginosa | BC 5923 | + | + |
| Pseudomonas aeruginosa | BC 5924 | + | + |
| Pseudomonas aeruginosa | BC 5925 | + | + |
| Pseudomonas aeruginosa | BC 5926 | + | + |
| Pseudomonas aeruginosa | BC 5927 | + | + |
| Pseudomonas aeruginosa | BC 5928 | + | + |
| Pseudomonas aeruginosa | BC 5929 | + | + |
| Pseudomonas aeruginosa | BC 5930 | + | + |
| Pseudomonas aeruginosa | BC 5932 | + | + |
| Pseudomonas aeruginosa | BC 5933 | + | + |
| Pseudomonas aeruginosa | BC 5934 | + | + |
| Pseudomonas aeruginosa | BC 7046 | + | + |
| Pseudomonas aeruginosa | BC 7047 | + | + |
| Pseudomonas aeruginosa | BC 7048 | + | + |
| Pseudomonas aeruginosa | BC 7049 | + | + |
| Pseudomonas aeruginosa | BC 7050 | + | + |
| Pseudomonas aeruginosa | BC 7051 | + | + |
| Pseudomonas aeruginosa | BC 7052 | + | + |
| Pseudomonas aeruginosa | BC 7053 | + | + |
| Pseudomonas aeruginosa | BC 7054 | + | + |
| Pseudomonas aeruginosa | BC 7055 | + | + |
| Pseudomonas aeruginosa | BC 7056 | + | + |
| Pseudomonas aeruginosa | BC 7057 | + | + |
| Pseudomonas aeruginosa | BC 7058 | + | + |
| Pseudomonas aeruginosa | BC 7059 | + | + |
| Pseudomonas aeruginosa | BC 7060 | + | + |
| Pseudomonas aeruginosa | BC 7061 | + | + |
| Pseudomonas aeruginosa | BC 7062 | + | + |
| Pseudomonas aeruginosa | BC 7063 | + | + |
| Pseudomonas aeruginosa | BC 7064 | + | + |
| Pseudomonas aeruginosa | BC 7065 | + | + |
| Pseudomonas aeruginosa | BC 7066 | + | + |
| Pseudomonas aeruginosa | BC 7067 | + | + |
| Pseudomonas aeruginosa | BC 7068 | + | + |
| Pseudomonas aeruginosa | BC 7069 | + | + |
| Pseudomonas aeruginosa | BC 7070 | + | + |
| Pseudomonas aeruginosa | BC 7071 | + | + |
| Pseudomonas aeruginosa | BC 7072 | + | + |
| Pseudomonas aeruginosa | BC 7073 | + | + |
| Pseudomonas aeruginosa | BC 7474 | n.p. | + |
| Pseudomonas aeruginosa | BC 7475 | n.p. | + |
| Pseudomonas aeruginosa | BC 8468 | n.p. | + |
| Pseudomonas aeruginosa | BC 8493 | n.p. | + |
| Pseudomonas alcaligenes | DSM 50342 | − | − |
| Pseudomonas asplenii | DSM 50254 | − | − |
| Pseudomonas cepacia | BC 3134 | − | − |
| Pseudomonas chloroaphis | BC 1753 | − | − |
| Pseudomonas citronellosis | DSM 50332 | − | − |
| Pseudomonas corrugata | DSM 7228 | − | − |
| Pseudomonas fluorescens | BC 950 | n.p. | − |
| Pseudomonas fluorescens | BC 4882 | − | − |
| Pseudomonas fluorescens | BC 2439 | − | − |
| Pseudomonas fragi | DSM 3456 | − | − |
| Pseudomonas indigofera | BC 1105 | n.p. | − |
| Pseudomonas mendocina | DSM 50017 | − | − |
| Psuedomonas oleovorans | DSM 1045 | − | − |
| Pseudomonas pickettii | BC 3323 | − | − |
| Pseudomonas pseudoalcaligenes | DSM 50188 | − | − |
| Pseudomonas putida | BC 4941 | − | − |
| Pseudomonas putida | DSM 291 | − | − |
| Pseudomonas putida | DSM 548 | − | − |
| Pseudomonas putida | DSM 549 | n.p. | − |
| Pseudomonas putida (ovalis) | ATCC 950 | − | − |
| Pseudomonas stutzeri | BC 4940 | − | − |
| Pseudomonas syringae | DSM 10604 | − | − |
| Citrobacter amalonaticus | DSM 4593 | − | n.p. |
| Enterobacter aerogenes | DSM 30053 | − | n.p. |
| Escherichia coli | ATCC 8739 | − | n.p. |
| Escherichia hermanii | DSM 4560 | − | n.p. |
| Klebsiella pneumoniae | BC 5362 | − | n.p. |
| Klebsiella terrigena | BC 4700 | − | n.p. |
| Proteus vulgaris | DSM 2024 | − | n.p. |
| Providencia stuartii | BC 5950 | − | n.p. |
| Salmonella Anatum | BC 2284 | − | n.p. |

BC: BioteCon strain collection; n.p.: not performed.

What is claimed is:

1. An isolated polynucleotide consisting of 30 contiguous nucleotides of SEQ ID NO: 1 or the complement thereof, wherein the polynucleotide optionally consists of a moiety that produces a signal or a binding site for a moiety that produces a signal when the polynucleotide hybridizes to *Pseudomonas* DNA.

2. An isolated polynucleotide consisting of SEQ ID NO: 3 or the complement of SEQ ID NO: 3, wherein the polynucleotide optionally consists of a moiety that produces a signal or a binding site for a moiety that produces a signal when the polynucleotide hybridizes to *Pseudomonas* DNA.

3. An isolated polynucleotide consisting of SEQ ID NO: 4 or the complement of SEQ ID NO: 4, wherein the polynucleotide optionally consists of a moiety that produces a signal or a binding site for a moiety that produces a signal when the polynucleotide hybridizes to *Pseudomonas* DNA.

4. An isolated polynucleotide consisting of SEQ ID NO: 5 or the complement of SEQ ID NO: 5, wherein the polynucleotide optionally consists of a moiety that produces a signal or a binding site for a moiety that produces a signal when the polynucleotide hybridizes to *Pseudomonas* DNA.

5. An isolated polynucleotide consisting of SEQ ID NO: 1 or the complement of SEQ ID NO: 1, wherein the polynucleotide optionally consists of a moiety that produces a signal or a binding site for a moiety that produces a signal when the nolynucleotide hybridizes to *Pseudomonas* DNA.

6. An isolated polynucleotide of any one of claims 1–5 which consists of a moiety that produces a signal or a binding site for a moiety that produces a signal when the polynucleotide hybridizes to *Pseudomonas* DNA.

7. A kit for detecting *Pseudomonas*, comprising one or more isolated polynucleotide(s) selected from the group consisting of SEQ ID No. 3, SEQ ID No. 4, SEQ ID No. 5, SEQ ID No. 1, 30 contiguous nucleotides of SEQ ID No. 1, and the complements thereof.

8. A method for detecting *Pseudomonas* in a sample, the method comprising the steps of
   (a) contacting the sample with a first polynucleotide comprising 10 or more contiguous nucleotides of SEQ ID No. 1, or the complement of SEQ ID No. 1, wherein the polynucleotide is 10–250 nucleotides long,
   (b) hybridizing said polynucleotide to *Pseudomonas* DNA in the sample, wherein hybridization detects *Pseudomonas* in the sample.

9. A method for detecting *Pseudomonas* in a sample, the method comprising amplifying *Pseudomonas* DNA in the sample using a first polynucleotide comprising 10 or more contiguous nucleotides of SEQ ID No. 1, or the complement of SEQ ID No. 1, wherein the first nolynucleotide is 10–250 nucleotides long, and a second polynucleotide comprising 10 or more contiguous nucleotides of i) SEQ ID No. 1, ii) the complement of SEQ ID No. 1, iii) the 23S gene, or iv) the 5S gene, wherein the second polynucleotide is 10–250 nucleotides long, thereby detecting *Pseudomonas* in the sample if amplification occurs.

10. A method for detecting *Pseudomonas* in a sample, the method comprising amplifying *Pseudomonas* DNA using a first polynucleotide and a second polynucleotide, wherein the first polynucleotide is SEQ ID No. 3 or SEQ ID No. 5 and the second polynucleotide is SEQ ID No. 2, thereby detecting *Pseudomonas* in the sample if amplification occurs.

11. The method of claim 8 wherein the first; polynucleotide further comprises a moiety that produces a signal or a binding site for a moiety that produces a signal when the polynucleotide hybridizes to *Pseudomonas* DNA.

12. The method of any one of claims 8–10, wherein the *Pseudomonas* is *Pseudomonas aeruginosa*.

13. The method of claim 8 wherein the first polynucleotide differentially hybridizes to DNA from different strains or species of *Pseudomonas*.

14. The method of claim 9 or 10 wherein the second polynucleotide differentially hybridizes to DNA from different strains or species of *Pseudomonas*.

15. A kit for detecting *Pseudomonas*, which comprises a polynucleotide of claim 6.

16. The kit of claim 7, wherein the polynucleotide is SEQ ID NO:4.

17. The method of claim 8 or 9, wherein the first polynucleotide comprises 15 to 30 contiguous nucleotides of SEQ ID No. 1, or the complement of SEQ ID No. 1.

18. A method for producing a primer or probe for detecting the presence of one or more *Pseudomonas* strain(s) that are to be detected in a sample, wherein the method comprises:
   a) performing a sequence alignment and sequence comparison to identify differences between the sequence of the 23S/5S intergenic region of genomic DNA isolated from one or more *Pseudomonas* strain(s) that are to be detected and the sequence of the 23S/5S intergenic region of genomic DNA isolated from one or more *Pseudomonas* strain(s) that are not to be detected; and
   b) producing a nucleic acid primer or probe comprising at least 15 contiguous nucleotides of SEQ ID NO:1, wherein the at least 15 continuous nucleotides differ in at least one nucleotide position between the sequence of the 23S/5S intergenic region of the *Pseudomonas* strain(s) that are to be detected and the sequence of the 23S/5S intergenic region of the *Pseudomonas* strain(s) that are not to be detected, wherein the primer or probe can be used for detecting the presence of the one or more *Pseudomonas* strain(s) that are to he detected.

19. The method of claim 18, wherein the 23S/5S intergenic region of genomic DNA has the sequence of SEQ ID NO:1.

20. The method of claim 18, wherein the 23S/5S intergenic region of genomic DNA has a sequence that is at least 90% homologous to SEQ ID NO:1.

21. The method of claim 18, wherein the 23S/5S intergenic region of genomic DNA comprises SEQ ID NO:5.

22. The method of claim 18, wherein the primer or probe comprises SEQ ID NO:3.

23. The method of claim 18, wherein the primer or probe comprises SEQ ID NO:4.

24. The method of claim 18, wherein the nucleic aced sequence of b) is at least 30 contiguous nucleotides.

25. The method of claim 18, wherein the nucleic acid primer or probe of b) is up to 250 nucleotides long.

26. The method of claim 18, wherein the nucleic acid sequence of b) is DNA.

27. The method of claim 18, wherein the nucleic acid sequence of b) is RNA.

28. The method of claim 18, wherein the nucleic acid sequence of b) is PNA.

* * * * *